United States Patent [19]
Zimmerman

[11] Patent Number: 5,577,514
[45] Date of Patent: Nov. 26, 1996

[54] CONDOM

[76] Inventor: Arnold S. Zimmerman, 17 Carbury Rd., Wayside, N.J. 07712

[21] Appl. No.: 574,600

[22] Filed: Dec. 18, 1995

[51] Int. Cl.⁶ .................................................. A61F 6/04
[52] U.S. Cl. ................................. 128/844; 128/918
[58] Field of Search ..................... 128/842, 844, 128/918; 604/347–353

[56] References Cited

U.S. PATENT DOCUMENTS 2,410,460 11/1946 Robinson ...................... 128/844
2,904,041 9/1959 Brown ......................... 128/844
4,446,860 5/1984 Gutnick ....................... 128/844
5,284,158 2/1994 Mallette ....................... 128/844

*Primary Examiner*—Michael A. Brown
*Attorney, Agent, or Firm*—Charles I. Brodsky

[57] ABSTRACT

A condom of a first diameter from its open end to a point approximately 4 cm from its closed end, where it enlarges to a second larger diameter, and preferably including a rupturable pocket inwardly formed in the condom from its closed end to enclose an antiseptic spermacidal solution which is released by thrusting penile movement within the condom.

15 Claims, 1 Drawing Sheet

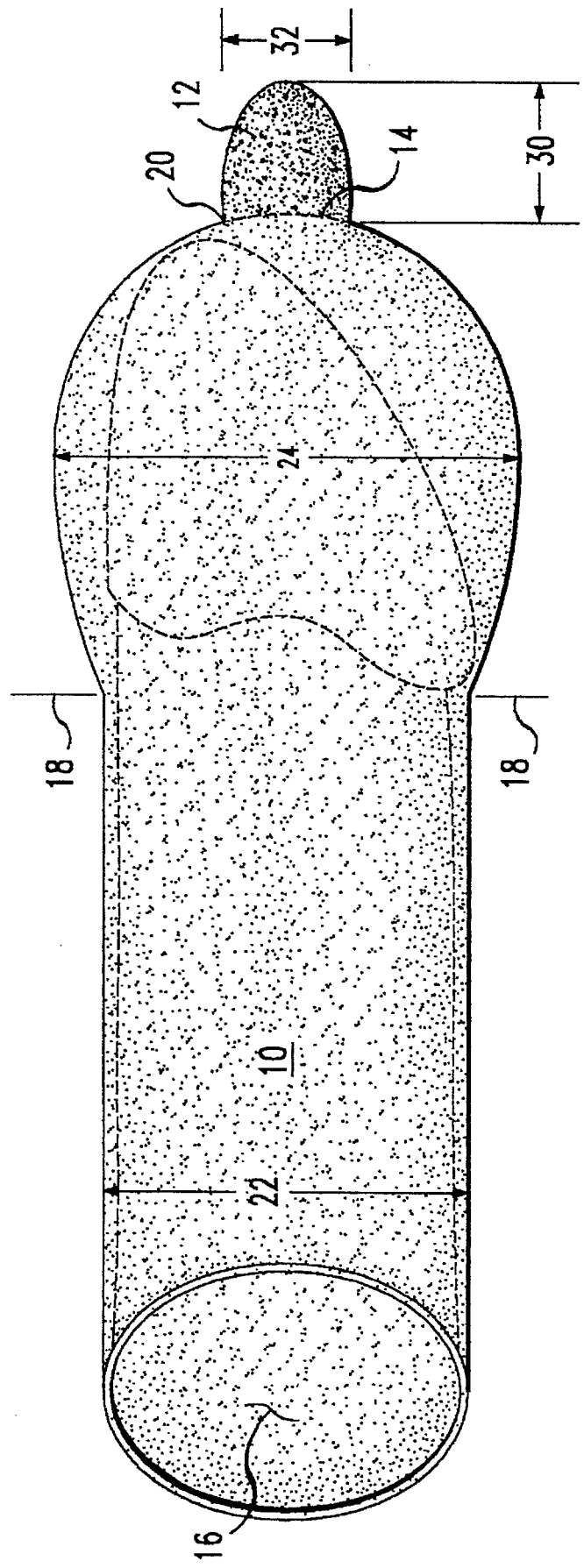

CONDOM

FIELD OF THE INVENTION

This invention relates to antiseptic, anti-viral solutions and, more particularly, to one which is additionally spermacidal in action. At the same time, this invention relates to a new condom design—and to one very specific design which utilizes the antiseptic, anti-viral spermacidal solution as a further contraceptive in the event of leaching of the condom.

BACKGROUND OF THE INVENTION

As is well known and understood, povidone iodine is very widely used for its antiseptic characteristics—either as a topical antiseptic, an antiseptic scrub, a surgical scrub, a vaginal douche and for similar such purposes. As has also been described, sugar is sometimes added to treat skin ulcers and pressure sores through the antibacterial characteristics of the sugar which reduces "water activity" to a level that is incompatible with bacteria growth. In those instances, in general, the formulation employed was one of 75% sugar, with some povidone-iodine added to it. These reported studies suggest that the anti-bacterial properties of honey or sugar make it useful as an aid in wound healing, in combination with an antiseptic formulation.

As is also well known and understood, many males shun the use of condoms because they are too constricting, too confining and reduce the sensations of sexual intercourse. Analysis has shown that this frequently follows because the condom must fit tightly to prevent its sliding off during penile movement. Frequently, in fact, the constriction literally chokes off the blood flow, and contributes to the losing of tumescence. Although promoted as a contraceptive and as a means of protecting against sexually transmitted diseases, condoms of the type available today do, in fact, leach and tear—sometimes allowing the very result they are intended to protect against.

OBJECTS OF THE INVENTION

It is an object of the present invention, therefore, to provide a new and improved condom which enhances the sensations of sexual intercourse, and which provides a further degree of protection should there be even a minor tear of the condom.

It is also an object of the invention to provide an antiseptic solution for use with such condom, which is also spermacidal so as to provide the degree of protection desired for the condom in the event of its tearing.

It is another object of the invention to provide such a solution which is anti-viral so as to permit its use in instances other than condom protection.

SUMMARY OF THE INVENTION

As will become clear from the following description, such an antiseptic, anti-viral, spermacidal solution follows from the combination of povidone iodine with sugar—but in a formulation different from that suggested in the literature, in that, according to this aspect of the invention, the povidone iodine, and not the sugar, is the major component of the resulting formulation. That is, the antiseptic, anti-bacteria characteristics of the previous compositions are maintained, but an anti-viral, spermacidal feature is added.

As will also become clear from the following description, such solution is particularly useful is the unique design, according to another aspect of the invention, of a condom which enhances sensation in use, by being of a first diameter along the length from its open end to a point short of reaching its closed end, wherein the diameter gradually increases about the penile glans. In such condom design, furthermore, a rupturable pocket is provided inwardly of the condom from its closed end, to enclose the antiseptic, anti-viral, spermacidal solution of the invention. Then, in the event of any tearing of the condom, or any leaching therefrom, the antiseptic, anti-viral solution further acts as a cidal to the sperm present in the semen ejaculation.

As will be understood from the following description, the antiseptic, anti-viral, spermacidal solution preferably comprises one ounce of undiluted povidone iodine, one teaspoon of granulated sugar, and a lubricant—with the strengths of the povidone iodine and the lubricant in solution forming to provide a concentration in the range of 0.25% to 0.50%. In a preferred embodiment of this solution, the lubricant will be seen to comprise a solution of polyethylene glycol—as, for example, wherein the povidone iodine is of a common type 10% in solution with twenty ounces of polyethylene glycol 400.

As will additionally be described below, the condom of the invention is of a given length from its open end to its closed end, and a first diameter from its open end to a point approximately 4 cm from the closed end, and of second, larger diameter, from that point to the closed end. In a preferred embodiment of the invention, the condom includes a rupturable pocket inwardly formed from the closed end, to be rupturable by a thrusting penile movement within the condom. In such pocket, the antiseptic, antiviral, spermacidal solution of the invention may be enclosed—and all together in a configuration where the increasing diameter of the condom extends a further 4 cm some 2 cm in from the rupturable pocket, i.e., in the general location of the penile glans.

BRIEF DESCRIPTION OF THE DRAWING

These and other features of the present invention will be more clearly understood from a consideration of the following description, taken in connection with the sole Figure of the drawing which illustrates a condom constructed in accordance with the above teachings.

DETAILED DESCRIPTION OF THE DRAWING AND OF THE INVENTION

Analysis, experimentation and testing has shown that a solution of povidone iodine, granulated sugar and a lubricant can be obtained in a concentration which is antiseptic, anti-viral and spermacidal. Further testing has shown that a preferred formulation is one where the strengths of the povidone iodine and the lubricant are selected to provide a concentration in the range of 0.25% to 0.50%, with a 0.50% concentration exhibiting very desirable characteristics when employing polyethylene glycol as the lubricant.

Commonly marketed under the name Batadine, the preparation is commonly obtained by heating povidone having an average molecular weight of 4,000 with elemental iodine in the presence of a little water, whereby a small amount of the iodine enters into loose organic union with the polymer to form a compound which typically contains approximately 9–12% of available iodine. In the preferred solution of the invention, a 10% solution has been found preferable.

The polyethylene glycol lubricant—or any other non-petroleum distillate having a small amount of glycerine in it, for that matter—may be of available 200, 300, 400 or 600 designation, although testing has indicated that polyethylene glycol 400 is preferable.

In accordance with the invention, the antiseptic, anti-viral, spermacidal solution is obtained by mixing one ounce of such undiluted povidone iodine 10% with one teaspoon of granulated sugar mixed with twenty ounces of polyethylene glycol 400.

Laboratory testing of the solution has shown it to be spermacidal, has shown it to forestall eruption and particular herpes on the skin and to be cidal to the AIDS virus—as well as to be useful as a topical antiseptic for healing and for wound treatment. The granulated sugar, in this usage, has been noted to increase the ability to "cling", by exhibiting a slight stickiness to adhere to other animate or inanimate objects.

The condom 10 of the drawing 10 includes this solution within a rupturable pocket 12 having a thin membrane 14 of a material rupturable by thrusting penile movement within the condom. Such "reservoir tip" 12 has been found to provide a predictable, pleasurable lubrication and sensation to the most sensitive part of the penis, the glans—and, as will be appreciated, provides additional protection against disease and pregnancy in the event the condom 10 breaks, or in the event it dislodges and falls off.

To further enhance the sexual sensation by allowing an unrestricted blood flow to the head of the penis, the condom 10 is of a first given length from its open end 16 to a point 18 approximately 4 cm from its closed end 20, where the membrane 14 is formed. That diameter—shown by the reference notation 22—gradually increases over the length from point 18 to the closed end 20, to reach a larger diameter 24 at the location of the glans, at approximately a further 4 cm, larger diameter. In this preferred embodiment, the distance back from the closed end 20 to the maximum increased diameter may be of the order of 2 cm, with another 2 cm being added as the condom length proceeds back to the point 18.

In this manner, the smaller diameter 22 for the condom 10 can be selected to restrict to the shaft of the penis in reducing any tendency for it to slip off, while the larger diameter 24 allows for the continued flow of blood to the head of the penis, to enhance sensation. In this preferred embodiment of the invention, the membrane 14 may be of a thin latex material which easily breaks with friction, so as to release the solution which is maintained in the pocket 12—constructed, for example, of a length 30 and of a height 32 both approximately 1 cm in dimension. As will be evident, the penile thrusting ruptures the membrane to release the spermacidal solution, so as to serve as a further protection against disease (because of the antiseptic, anti-viral characteristics), and as an additional protection against pregnancy in the event the condom tears (because of the spermacidal characteristics).

While there have been described what are considered to be preferred embodiments of the present invention, it will be appreciated that other modifications can be made by those skilled in the art without departing from the scope of the teachings herein. Thus, wherein the preferred condom embodiment of the invention has been described in the context of increasing the condom diameter beginning at a point some 4 cm from its closed end, it will be apparent that the gradual increase in diameter can begin at any selected point proximate to that closed end, and not necessarily beginning 4 cm away. And, similarly, the enlarged diameter increase of some 4 cm can be modified where desired, and the condom still provide the features set forth above. For at least such reasons, therefore, resort should be had to the claims appended hereto for a true understanding of the scope of the invention.

I claim:

1. A single layered condom of given length from its open end to its closed end, of a first diameter from said open end to a point approximately 4 cm from said closed end to restrict to the shaft of a penis in reducing any tendency for said condom to slip off, and of a second, larger diameter from said point to said closed end to allow for continued flow of blood to the head of the penis to enhance sensation.

2. The condom of claim 1, also including a rupturable pocket inwardly formed in said condom from said closed end, and enclosing a spermacidal solution.

3. The condom of claim 2, wherein said pocket encloses an antiseptic spermacidal solution.

4. The condom of claim 2, wherein said pocket includes a thin membrane of material rupturable by thrusting penile movement within said condom.

5. The condom of claim 1 gradually increasing in diameter from said point to approximately 4 cm greater than said first diameter.

6. The condom of claim 2, wherein said pocket encloses an antiseptic spermacidal solution comprising one ounce of povidone iodine, one teaspoon of granulated sugar, and a lubricant, with the strengths of said povidone iodine and said lubricant in solution forming to provide a concentration in the range of 0.25% to 0.50%.

7. The condom of claim 2, wherein said pocket encloses an antiseptic spermacidal solution comprising one ounce of povidone iodine 10% in solution and one teaspoon of granulated sugar, in solution with 20 ounces of polyethylene glycol 400 to provide a concentration of substantially 0.50%.

8. The condom of claim 1 gradually increasing in diameter from said point to a second point approximately 2 cm from said closed end, and gradually decreasing in diameter from said second point to said closed end.

9. The condom of claim 8 gradually increasing in diameter from said point to approximately 4 cm greater than said first diameter at said second point.

10. A condom of given length from its open end to its closed end, and of a first diameter from said open end to a point approximately 4 cm from said closed end, and of a second, larger diameter from said point to said closed end; also including a rupturable pocket inwardly formed in said condom from said closed end, and enclosing a spermacidal solution; and wherein said pocket encloses an antiseptic spermacidal solution comprising one ounce of povidone iodine, one teaspoon of granulated sugar, and a lubricant, with the strengths of said povidone iodine and said lubricant in solution forming to provide a concentration in the range of 0.25% to 0.50%.

11. The condom of claim 10 wherein said pocket includes a thin membrane of material rupturable by thrusting penile movement within said condom.

12. The condom of claim 10 gradually increasing in diameter from said point to approximately 4 cm greater than said first diameter.

13. The condom of claim 10 gradually increasing in diameter from said point to a second point approximately 2 cm from said closed end, and gradually decreasing in diameter from said second point to said closed end.

14. The condom of claim 13 gradually increasing in diameter from said point to approximately 4 cm greater than said first diameter at said second point.

15. A condom of given length from its open end to its closed end, and of a first diameter from said open end to a point approximately 4 cm from said closed end, and of a second, larger diameter from said point to said closed end; also including a rupturable pocket inwardly formed in said condom from said closed end, and enclosing a spermacidal solution; and wherein said pocket encloses an antiseptic spermacidal solution comprising one ounce of povidone iodine 10% in solution and one teaspoon of granulated sugar, in solution with 20 ounces of polyethylene glycol 400 to provide a concentration of substantially 0.50%.

* * * * *